(12) United States Patent
Burk et al.

(10) Patent No.: US 6,509,364 B2
(45) Date of Patent: *Jan. 21, 2003

(54) INTERPHENYLENE 7-OXABICYCLIC [2.2.1] HEPTANE OXAZOLES AS PROSTAGLANDIN $F_{2\alpha}$ ANTAGONISTS

(75) Inventors: Robert M. Burk, Laguna Beach, CA (US); Yariv Donde, Huntington Beach, CA (US); Michael E. Garst, Newport Beach, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/087,547

(22) Filed: Feb. 28, 2002

(65) Prior Publication Data

US 2002/0165399 A1 Nov. 7, 2002

Related U.S. Application Data

(63) Continuation of application No. 09/661,771, filed on Sep. 14, 2000, now Pat. No. 6,407,250.

(51) Int. Cl.⁷ .................. C07D 413/10; A61K 31/421
(52) U.S. Cl. .................. 514/374; 548/112; 548/236; 548/252
(58) Field of Search .................. 514/374; 548/112, 548/236, 252

(56) References Cited

U.S. PATENT DOCUMENTS

| | | |
|---|---|---|
| 4,632,928 A | 12/1986 | Rettegi et al. |
| 5,100,889 A | 3/1992 | Misra et al. |
| 5,153,327 A | 10/1992 | Misra et al. |
| 5,260,448 A | 11/1993 | Das et al. |
| 5,347,007 A | 9/1994 | Das et al. |
| 5,605,917 A | 2/1997 | Ogletree |
| 5,747,660 A | 5/1998 | Orlicky |
| 5,955,575 A | 9/1999 | Peri et al. |
| 6,407,250 B1 * | 6/2002 | Burk et al. .................. 548/112 |

FOREIGN PATENT DOCUMENTS

| | | |
|---|---|---|
| EP | 0 391 652 | 10/1990 |
| EP | 0 448 274 | 9/1991 |
| EP | 0 575 069 | 12/1993 |

OTHER PUBLICATIONS

Misra et al, "Interphenylene 7–Oxabicyclo[2.2.1]heptane Oxazoles. Highly Potent, Selective, and Long–Acting Thromboxane A2 Receptor Antagonists", J. Med. Chem. 1993, 36, 1401–1417.

Das et al, "Synthesis of Optically Active 7–Oxabicyclo [2.2.1]heptanes and Assignment of Absolute Configuration", Communications, Dec. 1987, 1100–1103.

* cited by examiner

Primary Examiner—Joseph K. McKane
Assistant Examiner—Golam M. M. Shameem
(74) Attorney, Agent, or Firm—Brent A. Johnson; Robert J. Baran; Martin A. Voet

(57) ABSTRACT

The present invention provides novel compounds represented by the general formula I.

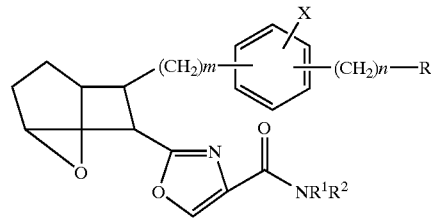

and pharmaceutically acceptable salts thereof wherein m, n, X, R, $R^1$ and $R^2$ are as defined in the specification. The novel compounds are $PGF_{2\alpha}$ antagonists, useful in pharmaceutical compositions for treating $PGF_{2\alpha}$-mediated disease responses such as inflammatory reactions relating to rheumatoid arthritis and psoriasis, reproductive disorders, bronchoconstrictive disorders (asthma), excessive bone breakdown (osteoporosis), peptic ulcers, heart disease, platelet aggregation and thrombosis.

17 Claims, 6 Drawing Sheets scheme 1

(a) CH₃I, DBU, acetone; (b) DIBAL, toluene -78 °C to rt; (c) PDC, MgSO₄, 4Å molecular sieves, CH₂Cl₂ 74% from 1; (d) Ph₃PCHCO₂CH₃, toluene 95%; (e) (Ph₃P)₃RhCl, H₂, EtOH 80%; (f) DIBAL, toluene -78 °C to rt 99%; (g) Dimethylthexylsilyl chloride, DMAP, Et₃N, CH₂Cl₂ 83%.

scheme 2

(a) Mg, THF, 65 °C; (b) EtMgBr, 0 °C to rt 69%; (c) Ac$_2$O, pyridine 77%; (d) (Im)$_2$S, ClCH$_2$CH$_2$Cl, 60 °C 94%; (e) n-Bu$_3$SnH, AIBN, toluene, 110 °C 84%; (f) CrO$_3$, H$_2$SO$_4$, acetone; (g) MeOH, AcCl 88% for 2 steps; (h) CrO$_3$, H$_2$SO$_4$, acetone.

scheme 3

(a) L-serine benzyl ester hydrochloride, DCC, HOBt, Et₃N, THF 80% for 2 steps;
(b) PPh₃, CCl₄, i-Pr₂NEt, CH₃CN 69%; (c) BrCCl₃, DBU, CH₂Cl₂ 0 °C 75%; (d) H₂, Pd(OH)₂/C, EtOAc 100%; (e) i. (COCl)₂, cat. DMF, CH₂Cl₂; ii. 4-cyclohexylbutylammonium chloride, Et₃N, CH₂Cl₂ 78%; (f) NaOH, aqueous THF, 95%.

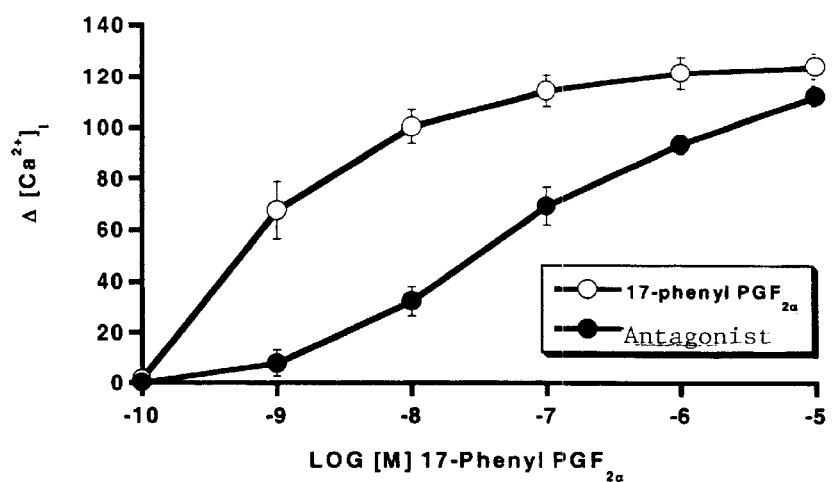
FIG. 4 Effect of 17-phenyl $PGF_{2\alpha}$ on FP receptor mediated $Ca^{2+}$ signaling in the absence (O) and presence (●) of the antagonist ($10^{-6}$ M); n = 4.

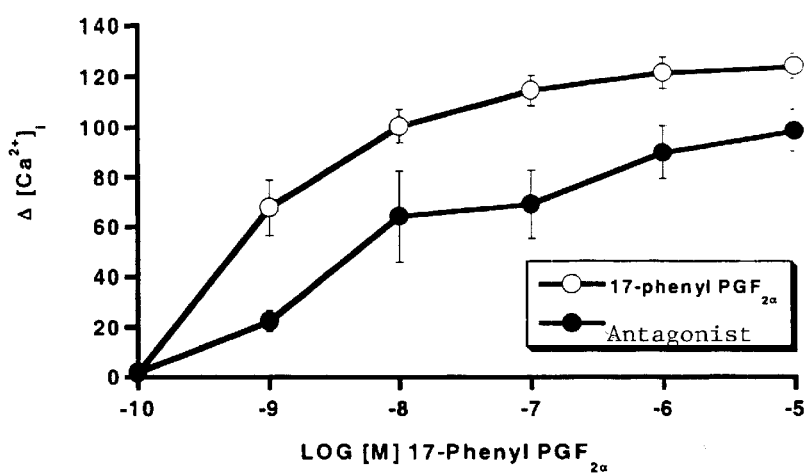
FIG. 5 Effect of 17-phenyl $PGF_{2\alpha}$ on FP receptor mediated $Ca^{2+}$ signaling in the absence (O) and presence (●) of antagonist ($10^{-5}$ M); n = 4.

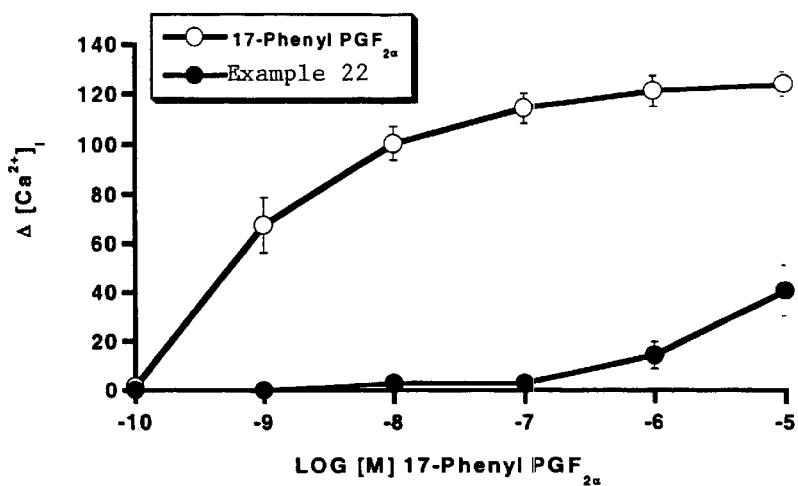
FIG. 6 Effect of 17-phenyl $PGF_{2\alpha}$ on FP receptor mediated $Ca^{2+}$ signaling in the absence (O) and presence (●) of the antagonist ($10^{-5}$ M); n = 4.

INTERPHENYLENE 7-OXABICYCLIC [2.2.1] HEPTANE OXAZOLES AS PROSTAGLANDIN $F_{2\alpha}$ ANTAGONISTS

CROSS REFERENCE TO RELATED APPLICATIONS

This patent application is a continuation of Ser. No. 09/661,771 U.S. Pat. No. 6,407,250 filed on Sep. 14, 2000. This patent application is related to a United States patent application Ser. No. 09/677,372, entitled INTERHETEROARYL 7-OXABICYCLIC [2.2.1]HEPTANE OXAZOLES AS PROSTAGLANDIN $F_{2\alpha}$ ANTAGONISTS which was also filed Sep. 14, 2000.

BACKGROUND OF THE INVENTION

1. Field of the Invention

The present invention provides novel Interphenylene 7-Oxabicyclo [2.2.1] heptane oxazoles useful as Prostaglandin $F_{2\alpha}$ (FP receptor) antagonists. The present invention also provides a method of synthesizing such novel compounds.

2. Description of Related Art

Prostaglandin $F_{2\alpha}$ antagonists are reported in U.S. Pat. Nos. 4,632,928; 5,747,660; and 5,955,575. The $PGF_{2\alpha}$ antagonists of U.S. Pat. No. 4,632,928 are pyrazole derivatives having an ergoline skeleton. The $PGF_{2\alpha}$ antagonist of U.S. Pat. No. 5,747,660 is a prostaglandin $F_{2\alpha}$ receptor regulatory protein (FPRP) which is able to inhibit the binding of $PGF_{2\alpha}$ to its receptor. The inventors of this patent state that the prostaglandin $F_{2\alpha}$ antagonist of their invention is believed to be the first selective prostaglandin $F_{2\alpha}$ antagonist discovered. U.S. Pat. No. 5,955,575 describes peptide sequences derived from the prostaglandin receptor $F_{2\alpha}$ and the G-protein, $G\alpha q$, as selective inhibitors of signal transduction involved in the stimulation of the prostaglandin receptor $F_{2\alpha}$.

Interphenylene 7-Oxabicyclo [2.2.1] heptane oxazoles, useful as Thromboxane $A_2$ receptor antagonists are reported in U.S. Pat. Nos. 5,100,889 and 5,153,327, European Patent Application 0 391 652 and J. Med. Chem. 1993, 36, 1401–1417.

Thromboxane $A_2$ receptor antagonists, e.g. 7-oxabicycloheptyl substituted heterocyclic amide prostaglandin analogs, alone, or in combination with anti-inflammatory agents are useful in treating ulcerative gastrointestinal conditions and dysmenorrhea as disclosed in European Patent Application 0 448 274 and U.S. Pat. No. 5,605,917.

BRIEF SUMMARY OF THE INVENTION

The invention relates to novel Interphenylene 7-Oxabicyclo [2.2.1] heptane oxazoles useful as $PGF_{2\alpha}$ antagonists, the synthesis thereof, and their use in treating diseases and conditions, where $PGF_{2\alpha}$ is involved.

The novel compounds of the present invention are represented by the general formula I.

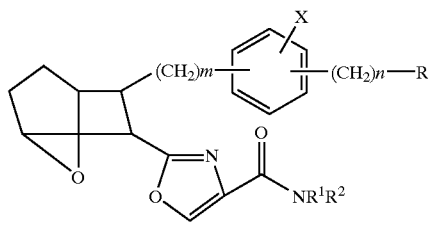

wherein
- m is an integer of from 1 to 3, preferably 1 or 2;
- n is 0 or an integer of from 1 to 4, preferably from 2 to 4;
- R is selected from the group Consisting Of $CO_2H$, $CO_2R^6$, $CH_2OH$, $CH_2OR^6$

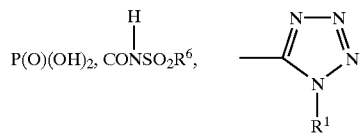

and $CONR^3R^4$;
- $R^1$ and $R^2$ are independently selected from the group consisting of H, $R^6$, $C_1$–$C_6$ alkenyl, $C_1$–$C_6$ alkynyl, $C_3$–$C_7$ cycloalkyl, $C_4$–$C_{12}$ alkylcycloalkyl, $C_6$–$C_{10}$aryl, $C_7$–$C_{12}$ alkylaryl radicals and heteroatom-substituted derivatives thereof, wherein one or more of the hydrogen or carbon atoms in said radicals is replaced with a halogen, nitrogen or sulfur-containing radical;
- $R^3$ and $R^4$ are independently selected from the group consisting of H and $R^6$; and X is selected from the group consisting of $R^6$, hydroxy, halogen, $COOR^6$, $NO_2$, $N(R^6)_2$, $CON(R^6)_2$, $SR^6$, sulfoxy, sulfone, CN and $OR^6$ wherein $R^6$ is $C_1$–$C_6$ alkyl, and pharmaceutically acceptable salts thereof.

These compounds are especially useful for treating a number of $PGF_{2\alpha}$-mediated disease responses. For instance, prostaglandins play an important role in inflammatory reactions relating to rheumatoid arthritis and psoriasis, reproductive disorders, bronchoconstrictive disorders (asthma), excessive bone breakdown osteoporosis), peptic ulcers, heart disease, platelet aggregation and thrombosis.

BRIEF DESCRIPTION OF THE DRAWINGS

FIG. 4 describes a dose response curve for the antagonist of U.S. Pat. Nos. 5,100,889 and 5,153,327.

FIG. 5 describes a dose response curve for the 1-methyl ester of the antagonist of U.S. Pat. Nos. 5,100,889 and 5,153,327.

FIG. 6 describes a dose response curve for the compound of Example 22, below.

DETAILED DESCRIPTION OF THE INVENTION

Preferably, the novel interphenylene 7-oxabicyclo [2.2.1] heptane oxazole compounds are represented by the general formula II.

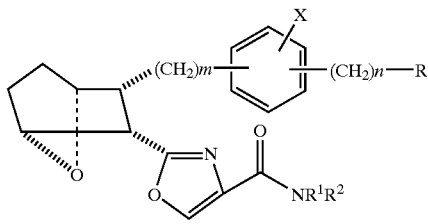

Preferably, R is selected from the group consisting of $CO_2H$, $CO_2R^6$, $CH_2OH$, $CH_2OR^6$ and $CONR^3R^4$.

More preferably R is selected from the group consisting of $CO_2H$ and $CO_2R^6$, e.g. $CO_2H$ and $CO_2CH_3$.

Preferably, $R^1$ and $R^2$ are selected from the group consisting of H, $R^6$, $C_3$–$C_7$ cycloalkyl and $C_4$–$C_{12}$ alkylcycloalkyl.

Preferably X is selected from the group consisting of halogen, e.g. fluoro.

More preferably, the novel compounds of the present invention are represented by the general formula III.

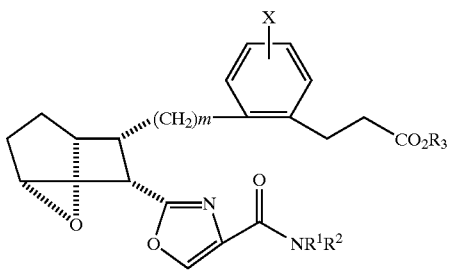

For the compounds of formula III, X is preferably F and $R^3$ is preferably H or $CH_3$.

Figure 1:
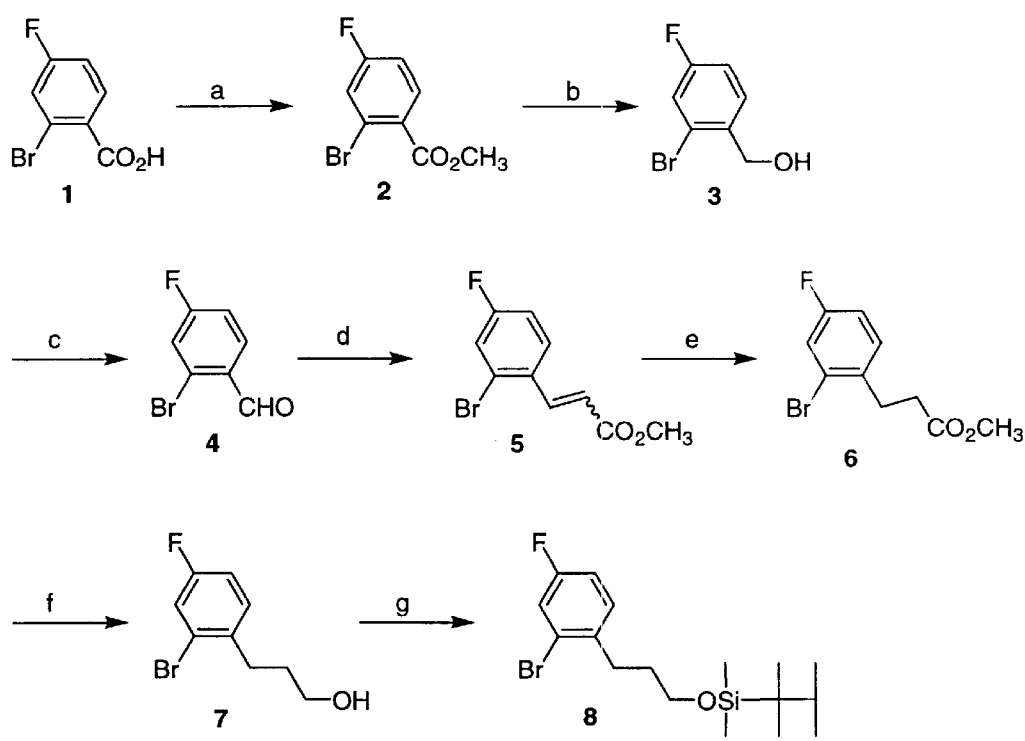
FIG. 1 describes the synthesis of a silylether intermediate, prepared according to Examples 1 through 8, below, and useful in the preparation of the novel compounds of the invention.
Figure 2:
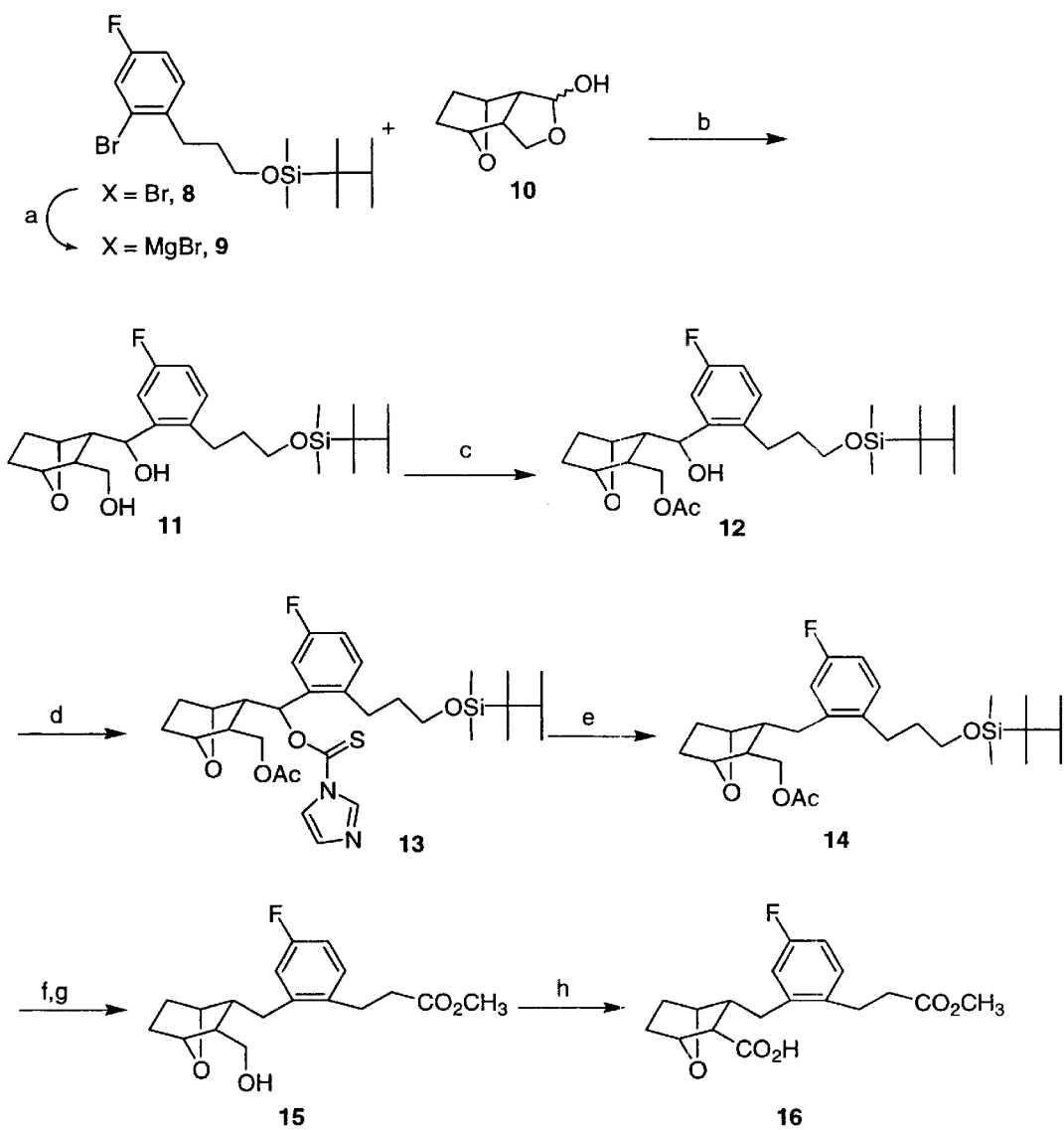
FIG. 2 describes the synthesis of an acetate intermediate, prepared according to Examples 9 through 14, below, and useful in the preparation of the novel compounds of the invention.
Figure 3:
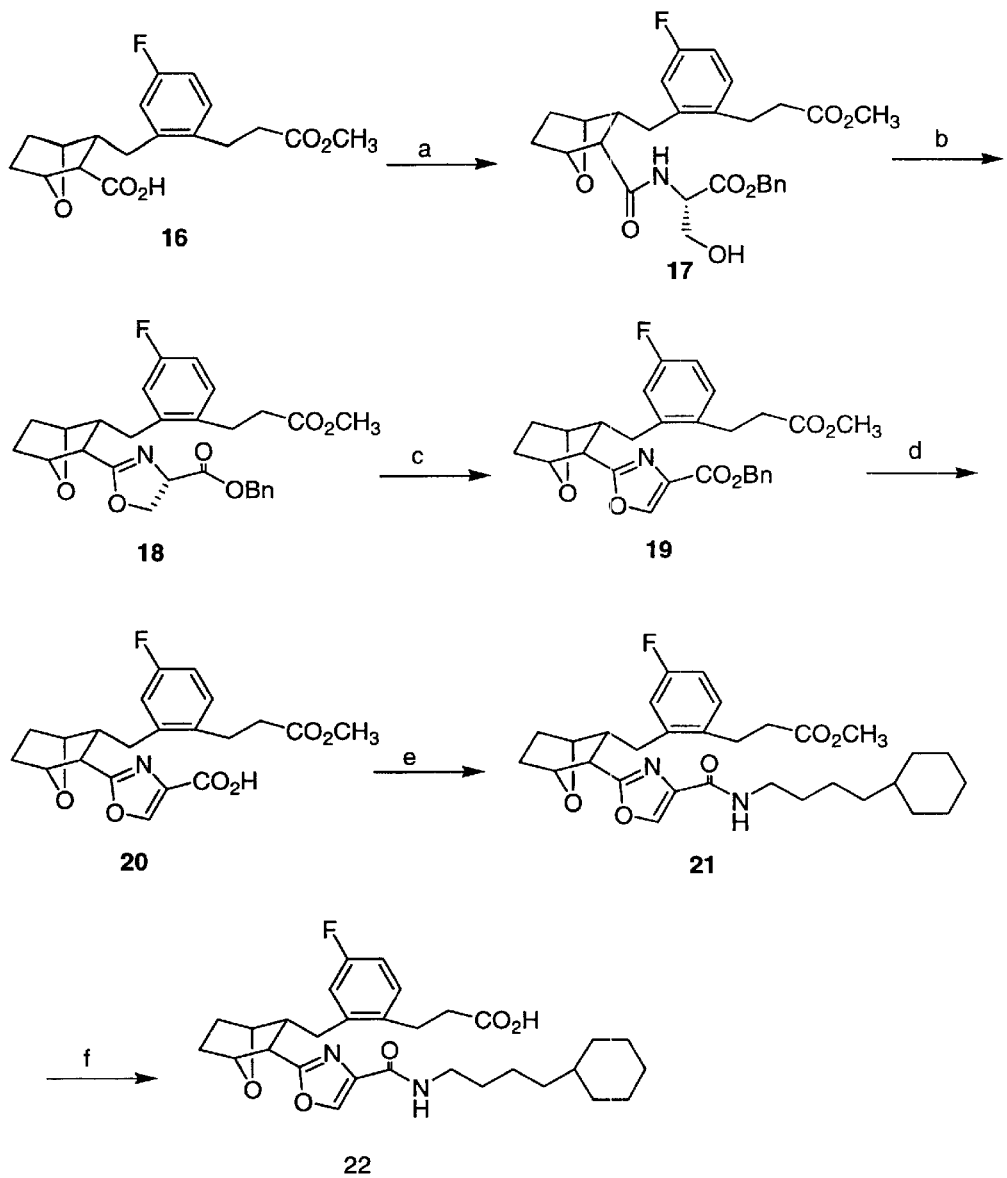
FIG. 3 describes the synthesis of one of the novel compounds of the present invention, prepared according to Examples 16 through 21, below.

The following Examples describe a method of synthesizing the novel compounds of the invention wherein the numbering of the Examples corresponds to the numbering of the various intermediates and final compounds shown in FIGS. 1 through 3.

EXAMPLE 1

2-Bromo-4-fluorobenzoic acid. The named compound is purchased from Marshallton Research Laboratories Inc., P.O. Box 930, King, N.C. 27021.

EXAMPLE 2

2-Bromo-4-fluorobenzoic acid, methylester. A solution of 2-bromo-4-fluorobenzoic acid (5 g, 22.8 mmol), DBU (5.21 g, 34.2 mmol), and methyl iodide (6.48 g, 45.7 mmol) in acetone (23 mL) was stirred at room temperature for 2 h. The reaction was concentrated in vacuo and the residue partitioned between EtOAc and 1 M HCl. The organic portion was washed with saturated aqueous $NaHCO_3$, brine and then was dried ($MgSO_4$), filtered and evaporated to give the ester of Example 2 (5.18 g) which was used directly in the next step.

EXAMPLE 3

(2-Bromo-4-fluorophenyl)methanol. DIBAL-H (56 mL, 56 mmol, 1M/toluene) was added to a solution of the ester of Example 2 (5.18 g, 22.2 mmol) in toluene (50 mL) at −78° C. After 1 h, the reaction was warmed to room temperature and quenched by dropwise addition of 1 M NaOH. The mixture was extracted with EtOAc. The organic portion was washed with brine and then was dried (MgSO4), filtered, and evaporated to give the alcohol of Example 3 (4.55 g) which was used directly in the next step.

EXAMPLE 4

2-Bromo-4-fluorobenzaldehyde. A mixture of the alcohol of Example 3 (4.55 g, 22.2 mmol), PDC (10.0 g, 26.6 mmol), $MgSO_4$ (10.0 g) and crushed 4 Å molecular sieves (10.0 g) in $CH_2Cl_2$ (44 mL) was stirred for 12 h. The mixture was diluted with ether and filtered through celite. The solvent was evaporated and the residue purified by flash column chromatography on silica gel (10% EtOAc/hexanes) to give the aldehyde of Example 4 (3.43 g, 16.9 mmol, 74% from 2-bromo-4-fluorobenzoic acid).

EXAMPLE 5

(E)-3-(2-Bromo-4-fluorophenyl)acrylic acid methyl ester. A mixture of the aldehyde of Example 4 (4.5 g, 22.2 mmol) and methyl(triphenylphosphoranylidene)acetate (8.91 g, 36.6 mmol) in toluene (22 mL) was stirred for 12 h. The solvent was removed in vacuo and the residue was purified by flash column chromatography on silica gel (5% EtOAc/hexanes) to give the ester of Example 5 (5.46 g, 21.1 mmol, 95%).

EXAMPLE 6

3-(2-Bromo-4-fluorophenyl)propionic acid methyl ester. A mixture of $(Ph_3P)_3RhCl$ (1.49 g, 1.61 mmol) and the ester of Example 5 (4.17 g, 16.1 mmol) in ethanol (30 mL) was evacuated and purged with $H_{2(g)}$. The mixture was stirred under 1 atm $H_2$ pressure for 12 h. The solvent was removed in vacuo and the residue was purified by flash column chromatography on silica gel (5% EtOAc/hexanes) to give the ester of Example 6 (3.50 g, 13.4 mmol, 80%).

EXAMPLE 7

3-(2-Bromo-4-fluorophenyl)propan-1-ol. A −78° C. solution of the ester of Example 6 (3.50 g, 13.4 mmol) in toluene (20 mL) was treated dropwise with DIBAL-H (33.5 mL, 33.5 mmol, 1 M/toluene). After 1 h, the reaction was warmed to room temperature and then was quenched with dropwise addition of 1 M $H_2SO_4$. The warm mixture was poured onto ice and extracted with EtOAc. The organic portion was washed with saturated aqueous $NaHCO_3$, brine and then was dried ($MgSO_4$), filtered, and evaporated. Purification by flash column chromatography on silica gel (25% EtOAc/hexanes) gave the alcohol of Example 7 (3.09 g, 13.3 mmol, 99%).

EXAMPLE 8

[3-(2-Bromo-4-fluoro-phenyl)-propoxyl]dimethyl-(1,1,2-trimethyl-propyl)silane. A solution of the alcohol of Example 7, (2.1 g, 9.0 mmol), dimethylthexylsilyl chloride (2.8 mL, 14.2 mmol, Aldrich), $Et_3N$ (1.36 mL, 9.76 mmol, Aldrich) and 4-(dimethylamino)pyridine (48 mg, 0.39 mmol, Aldrich) in $CH_2Cl_2$ (16 mL, Aldrich) was stirred for 18 h. The solution was poured into saturated aqueous $NaHCO_3$ solution (25 mL) and the mixture extracted with $CH_2Cl_2$ (2×25 mL). The combined $CH_2Cl_2$ solution was dried ($MgSO_4$), filtered, evaporated and purified by flash column chromatography on silica gel(2% EtOAc/ hexanes→30%→40%) to give the silane of Example 8 (2.792 g, 7.4 mmol, 83%).

EXAMPLE 9

A mixture of Mg turnings (173 mg, 7.1 mmol, Aldrich), iodine (2 crystals), and 1,2-dibromoethane (20 μL) in dry THF (2.6 mL, Aldrich) was heated in a 64° C. oil bath with magnetic stirring until the iodine color disappeared (ca. 15 min.). The resulting mixture was allowed to cool to room temperature and a solution of the bromide of Example 8 (1.882 g, 5.0 mmol) in 1.5 mL THF was added dropwise via cannula, rinsing with 1 mL THF. The mixture was heated in the 64° C. oil bath for 3 h, allowed to cool to room temperature and used directly in the next step.

EXAMPLE 10

3aR-(3aα, 4α, 7α, 7aα)]-1-Hydroxyhexahydro-4,7-epoxyisobenzofuran. The named compound is prepared according to Das, J.; Haslanger, M. F.; Gougougoutas, J. Z.; Malley, M. F. Synthesis of Optically Active 7-Oxabicyclo[2.2.1]heptanes and Assignment of Absolute Configuration. Synthesis 1987, 1100–1103 except in the final DIBAL-H reduction of the corresponding lactone, the reaction was quenced with methanol and worked up with aqueous 1N NaOH.

EXAMPLE 11

1-(2-{3-[Dimethyl-(1,1,2-trimethyl-propyl)-silanyloxy]-propyl}-5-fluoro-phenyl)-1-((1R, 2S, 3R, 4R-3-hydroxymethyl-7-oxa-bicyclo[2.2.1]hept-2-yl)-methanol. An ice-cold solution of lactol 10 (3aR-(3aα, 4α, 7α, 7aα)]-1-Hydroxyhexahydro-4,7-epoxyisobenzofuran (708 mg, 4.53 mmol) in 2.4 mL of dry THF (Aldrich) was treated dropwise with EtMgBr (4.5 mL, 4.5 mmol, 1 M/THF, Aldrich). After 20 min., the Grignard solution from Example 9 above was added via cannula and the solution allowed to warm to room temperature.

After 16 h, the reaction was quenched by addition of 2.8 mL of saturated aqueous NH₄Cl solution with cooling. The resulting mixture was stirred for 2 h and then CH₂Cl₂ (10 mL) was added. The solution was decanted from the gum, the gum washed further with CH₂Cl₂ (3×10 mL), and the combined CH₂Cl₂ solution was dried (MgSO₄), filtered, and evaporated. Purification of the crude product by flash column chromatography on silica gel (40% EtOAc/hexanes) gave the diol of Example 11 (1.386 g, 3.1 mmol, 69%) as an oil.

EXAMPLE 12

Acetic acid (1R, 2R, 3S, 4R)-3-[1-(2-{3[dimethyl-(1,1,2-trimethyl-propyl)-silanyloxy]-propyl}-5-fluoro-phenyl)-1-hydroxy-methyl]-7-oxa-bicyclo[2.2.1]hept-2-ylmethyl ester. The diol of Example 11 (713 mg, 1.62 mmol) was co-evaporated with benzene (2×2 mL). The residue was taken into 1.5 mL of dry pyridine (Aldrich) and was treated with Ac₂O (195 μL, 2.07 mmol, Aldrich). The solution was allowed to stir for 17 h and then was evaporated and co-evaporated twice with toluene. Flash column chromatography on silica gel (20% EtOAc/hexanes→30%→40%→50%) gave the monoacetate of Example 12 (564 mg, 1.17 mmol, 72%).

EXAMPLE 13

Acetic Acid (1R, 2R, 3R, 4R)-3-[1-(2-{3-[dimethyl-(1,1,2-trimethyl-propyl)-silanyloxy]-propyl}-5-fluoro-phenyl)-1-(1-imadazol-1-yl-methanethioyloxy)-methyl]-7-oxa-bicyclo[2.2.1]hept-2-ylmethyl ester. The acetate of Example 12 (5.64 mg, 1.17 mmol) was co-evaporated with benzene (2×2 mL). The residue was taken into dry dichloroethane (0.8 mL, Aldrich) and 1,1'-thiocarbonyldiimidazole (643 mg, 3.61 mmol, Aldrich) was added. The mixture was heated in a 60° C. oil bath with stirring. After 1 h, there was a considerable amount of starting material and so the solvent level was reduced under a nitrogen stream and the reaction allowed to stir further for another 1 h at which time the reaction was complete (TLC analysis). The mixture was allowed to cool to room temperature and then purified by flash column chromatography on silica gel (30% EtOAc/hexanes→40%) which gave the ester of Example 13 (506 mg, 0.93 mmol, 79%).

EXAMPLE 14

Acetic acid (1R, 2R, 3R, 4R)-3-(2-{3-[dimethyl-(1,1,2-trimethyl-propyl)-silanyloxy]-propyl}-5-fluoro-benzyl)-7-oxa-bicyclo[2.2.1]hept-2-ylmethyl ester. A solution of the ester of Example 13 (506 mg, 0.93 mmol), Bu₃SnH (1.44 mL, 5.35 mmol, Aldrich), and AIBN (53 mg, 0.32 mmol, Alfa) in toluene (45 mL, Aldrich) was heated in a 110° C. oil bath. After 2 h, the reaction was not complete (TLC analysis) and so another 53 mg of AIBN was added. After 1 h of further heating the reaction was complete. The solution was allowed to cool to room temperature, was evaporated and then purified by flash column chromatography on silica gel (100% hexanes→5% EtOAc/hexanes→10%) which gave the ester of Example 14 (366 mg, 0.78 mmol, 84%).

EXAMPLE 15

3-[4-Fluoro-2-((1R, 2R, 3R, 4R)-3-hydroxymethyl-7-oxa-bicyclo[2.2.1]hept-2-ylmethyl)-phenyl]-propionic acid methyl ester. A solution of the ester of Example 14 (577 mg, 1.2 mmol) in acetone (6 mL, B & J brand) was treated dropwise with Jones reagent (0.84 mL, 2.5 M in Cr(VI), 2.1 mmol). After 20 min., the reaction was quenched by addition of isopropyl alcohol (0.5 mL). The mixture was allowed to stir for 15 min. and then was filtered through celite. The filtrate was evaporated and the residue was partitioned between CH₂Cl₂ (20 mL) and 3:1 H₂O/brine (20 mL). The aqueous portion was further extracted with CH₂Cl₂ (2×20 mL) and the combined CH₂Cl₂ solution dried (MgSO₄), filtered and evaporated to leave the acid as a slightly yellow oil that was used directly in the next step.

The crude acid was taken into a solution of 1% v/v AcCl/MeOH (3.5 mL). After 20 h, NaHCO₃ (110 mg) was added and the mixture diluted with diethyl ether (20 mL). The mixture was dried (MgSO₄), filtered, evaporated, and purified by flash column chromatography on silica gel (60% EtOAc/hexanes→67%→75%) which gave 15 3-[4-Fluoro-2-((1R,2R,3R,4R)-3-hydroxymethyl-7-oxa-bicyclo[2.2.1]hept-2-ylmethyl)-phenyl]-propionic acid methyl ester (339 mg, 1.05 mmol) in 88% yield from the ester of Example 14.

EXAMPLE 16

(1R, 2S, 3R, 4R)-3-[5-fluoro-2-(2-methoxycarbonyl-ethyl)-benzyl]phenyl)-7-oxa-bicyclo[2.2.1]heptane-2-carboxylic acid. A solution of the ester of Example 15 (336 mg, 1.04 mmol) in acetone (8 mL, B & J brand) was treated dropwise with Jones reagent (0.8 mL, 2.0 mmol, 2.5 M). The orange mixture was allowed to stir for 35 min. and then was quenched by addition of 0.5 mL isopropyl alcohol. After 15 min., the mixture was filtered through celite and evaporated. The residue was partitioned between 10 mL 1 M HCl and 20 mL CH$_2$Cl$_2$. The aqueous layer was extracted further with CH$_2$Cl$_2$ (2×20 mL) and the combined CH$_2$Cl$_2$ solution dried (MgSO$_4$), filtered and evaporated to give crude 16 (338 mg, 1.00 mmol, 97%).

EXAMPLE 17

(S)-2[(1-{(1R, 2S, 3R, 4R)-3-5-fluoro-2-(2-methoxycarbonyl-ethyl)-benzyl]-7-oxa-bicyclo[2.2.1]hept-2-yl}-methanoyl)-amino]-3-hydroxy-propionic acid benzyl ester. The crude acid 16 (338 mg, 1.00 mmol, ) was co-evaporated with benzene and the residue was taken into dry THF (4.3 mL, Aldrich). The solution was cooled in an ice bath and 1-hydroxybenzotriazole monohydrate (188 mg, 1.39 mmol, Aldrich), L-serine benzyl ester hydrochloride (259 mg, 1.12 mmol, Sigma), and triethylamine (0.31 mL, 2.22 mmol, Aldrich) were added. The mixture was stirred for 5 min. and DCC (233 mg, 1.13 mmol, Aldrich) in THF (0.5 mL) was added, followed with rinsing the sides of the flask with 0.5 mL of THF. The mixture was allowed to slowly warm to room temperature.

After 18 h, the mixture was cooled in an ice bath and ethyl acetate (4.3 mL) was added. The resulting mixture was filtered, evaporated and purified by flash column chromatography on silica gel (100% ethyl acetate) which gave slightly impure product (475 mg). Recrystallization (hexanes/ethyl acetate) gave the pure amide of Example 17 (176 mg, 0.34 mmol, 34%).

EXAMPLE 18

(S)-2-{(1R, 2S, 3R, 4R)-3-[5-2-(2-methoxycarbonyl-ethyl)-benzyl]-7-oxa-bicyclo[2.2.1]hept-2-yl{-4,5-dihydro-oxazole-4-carboxylic acid benzyl ester. PPh$_3$ (120 mg, 0.46 mmol, Aldrich) and i-Pr$_2$NEt (82 µL, 0.47 mmol, Aldrich) were added to a solution of the amide of Example 17 (153 mg, 0.30 mmol) in dry CH$_2$Cl$_2$ (0.26 mL, Aldrich) and dry CH$_3$CN (1.0 mL, Aldrich). CCl$_4$ (43 µL, 0.45 mmol, Aldrich) was added dropwise and after 4 h of stirring, the solution was cooled in an ice bath and ethyl acetate (3 mL) and saturated aqueous NaHCO$_3$ solution (1 mL) were added. The mixture was poured into saturated aqueous NaCl solution (10 mL) and was extracted with ethyl acetate (10 mL). The organic portion was washed with saturated aqueous NaCl solution (10 mL) and then was dried (MgSO$_4$), filtered, evaporated and purified by flash column chromatography on silica gel (2:1 EtOAc/hexanes) to give the oxazoline of Example 18 (102 mg, 0.21 mmol, 69%).

EXAMPLE 19

2-{(1R, 2S, 3R, 4R)-3-[5-fluoro-2-(2-methoxycarbonyl-ethyl)-benzyl]-7-oxa-bicyclo[2.2.1]hept-2-yl}-oxazole-4-carboxylic acid benzyl ester. The oxazoline of Example 18 was co-evaporated with benzene and then taken into dry CH$_2$Cl$_2$ (1 mL, Aldrich). The solution was cooled in an ice bath and DBU (30 µL, 0.20 mmol, Aldrich) and BrCCl$_3$ (19 µL, 0.19 mmol, Aldrich) were added. The solution was allowed to stand at 0° C. for 17 h and then was diluted with CH$_2$Cl$_2$ (10 mL). The CH$_2$Cl$_2$ solution was washed with saturated aqueous NH$_4$Cl solution (2×5 mL) and the combined aqueous solution extracted with EtOAc (2×10 mL). The combined organic solution was dried (MgSO$_4$), filtered, evaporated, and purified by flash column chromatography on silica gel (40% ethyl acetate/hexanes) to give the oxazole of Example 19 (74 mg, 0.15 mmol, 75%).

EXAMPLE 20

2-{(1R, 2S, 3R, 4R)-3-[5-fluoro-2-(2-methoxycarbonyl-ethyl)-benzyl]-7-oxa-bicyclo[2.2.1]hept-2-yl}-oxazole-4-carboxylic acid. Pd(OH)$_2$/C (17 mg, 20%, Aldrich) was added to a solution of the oxazole of Example 19 (74 mg, 0.15 mmol) in ethyl acetate (1.4 mL, B & J brand). The mixture was stirred under a balloon of H$_{2(g)}$ for 2 h and then was filtered through celite. Evaporation of the ethyl acetate left the acid of Example 20 (63 mg, 0.16 mmol, 100%) as a white crystalline solid.

EXAMPLE 21

3-(2-{(1R, 2R, 3S, 4R)-3-[4-(4-Cyclohexyl-butylcarbamoyl)-oxazol-2-yl]-7-oxa-bicyclo[2.2.1]hept-2-ylmethyl)-4-fluoro-phenyl)-propionic acid methyl ester. The acid of Example 20 (26 mg, 0.064 mmol) was co-evaporated with benzene and the residue taken into dry CH$_2$Cl$_2$ (0.3 mL, Aldrich). Dry DMF (small drop, Aldrich) was added followed by (COCl)$_2$ (11 µL, 0.13 mmol, Aldrich) which caused immediate gas evolution. After 30 min., the volatiles were removed and the residue co-evaporated twice with toluene to leave an off-white solid.

The crude acid chloride was taken into dry CH$_2$Cl$_2$ (0.36 mL, Aldrich) and Et$_3$N (21 µL, 0.15 mmol, Aldrich) was added. 4-cyclohexylbutylammonium chloride (18 mg, 0.094 mmol) was then added and the reaction stirred for 1.5 h. The mixture was partitioned between 10 mL EtOAc and 10 mL 1 M HCl. The aqueous layer was extracted with 10 mL EtOAc and the combined EtOAc solution dried (MgSO$_4$), filtered, evaporated, and purified by flash column chromatography on silica gel (50% EtOAc/hexanes) to give the ester of Example 21 (27 mg, 0.05 mmol, 78%) as a white solid.

EXAMPLE 22

3-(2-{(1R, 2R, 3S, 4R)-3-[4-(4-Cyclohexyl-butylcarbamoyl)oxazol-2-yl]-7-oxa-bicyclo[2.2.1]hept-2-ylmethyl}-4-fluoro-phenyl)-propionic acid. A solution of the ester of Example 21 (26 mg, 0.048 mmol) in THF (0.15 mL, Aldrich) and MeOH (0.75 mL, B&J Brand) was treated with 1 M NaOH solution (0.29 mL, 0.29 mmol). After 17 h, The solution was partitioned between 10 mL CH$_2$Cl$_2$ and 10 mL 1 M HCl. The aqueous layer was extracted with CH$_2$Cl$_2$ (2×10 mL) and the combined CH$_2$Cl$_2$ solution dried (MgSO$_4$), filtered, evaporated, and purified by flash column chromatography on silica gel (5% MeOH/CH$_2$Cl$_2$) to give the oxazole of Example 22 (24 mg, 0.046 mmol, 95%) as a white solid.

500 MHz $^1$H NMR (CDCl$_3$, ppm) δ8.13 (s, 1H) 7.11–7.08 (m, 2H) 6.85–6.80 (m, 2H) 4.97 (d, J=4.4 Hz, 1H) 4.37 (d, J=4.8 Hz, 1H) 3.4–3.3 (m, 3H) 2.84 (t,J=7.7 Hz, 2H) 2.6–2.5 (overlapping m, 3H) 2.35 (dd, J=14.5, 11.2 Hz, 1H) 2.20 (dd, J=14.5, 4.9 Hz, 1H) 1.9–1.1 (overlapping m, 20H) 0.9–0.8 (m, 2H). MS (EI) m/z 526.2831 (526.2843 calculated for C$_{30}$H$_{39}$FN$_2$O$_5$; error=2 ppm).

The compound of Example 22 was tested for PGF$_{2\alpha}$ antagonist activity as follows:

Ca$^{2+}$ SIGNALING

HEK cells stably transfected with the human FP receptor were removed rom the culture flasks by approximately 1 min treatment with trypsin 0.05%/0.53 mM EDTA in HBSS (Gibco, Grand Island, N.Y.) at 37° C. Proteolytic activity was arrested by adding 5 ml of 10% fetal bovine serum in DMEM. The cells were consecutively washed in Hank's BSS and medium containing 140 mM NaCl, 50 mM KCl, 1 mM MgCl$_2$, 1.5 mM CaCl$_2$, 10 mM HEPES: TRIS, 5 mM glucose, 5 mM Na pyruvate, 0.1% bovine serum albumin at pH 7.4: centrifugation for the washes was performed for 15 minutes at 200 g at room temperature. Cells were counted, resuspended in the above medium and incubated with 2×10$^{-6}$ M Fura 2/acetoxymethyl ester in a shaking water bath for 30 minutes at 37° C. The cells were subsequently washed in medium as above and resuspended at a concentration of $2\times10^{-6}$ cells ml$^{-1}$. Aliquots of 0.5 ml cell suspension were then added to autocap microtubes to provide $10^6$ cells per experimental determination of intracellular free $Ca^{2+}$ concentration ($[Ca^{2+}]_i$).

Fluorescence was measured in a Perkin-Elmer LS-5 fluorescence spectrophotometer at excitation and emission wavelengths of 340 and 492 nm, respectively, with both slits at 10 nm. For each experimental determination $10^6$ cells were washed (200×g for 5 min) and suspended in a 2 ml cuvette with buffer containing 120 mM NaCl, 6 mM KCl, 1 mM MgSO$_4$, 1.5 mM CaCl$_2$, 20 mM HEPES, 1 mg ml$^{-1}$ glucose and 1 mg ml$^{-1}$ Na pyruvate. Stirring was achieved by an overhead-mounted, paddle stirrer with the temperature maintained at 37° C. The cells were lysed with digitonin (10 $\mu$l of 100 mg ml$^{-1}$ DMSO) to obtain $f_{max}$. EGTA (100 mM) and sufficient 10N NaOH to adjust the pH to 8.5 were then successively added to obtain $f_{min}$.

As shown in the Table, below, the compound of Example 22 has PGF$_{2\alpha}$ antagonist activity that is greater than the compound disclosed in U.S. Pat. Nos. 5,100,889 and 5,153,327, above. Also to be noted that small changes, such as converting the compound of the patents to the 1-methyl ester, greatly effects activity. That is the 1-methyl ester is much less active than the corresponding acid.

These compounds exert their antagonist effects by competing with agonist, in this case 17-phenyl PGF$_{2\alpha}$ for the FP receptor.

The recombinant human FP receptor has been used in these studies. It is the authenticated target FP receptor. The cat iris is not an appropriate assay for such studies for the following reasons. The cat iris is very responsive to both acidic and neutral PGF$_{2\alpha}$ analogs and, for this reason, the above antagonist compounds exhibit much weaker activity in this preparation.

The compounds of the invention can be administered orally or parenterally to various mammalian species known to be subject to PGF$_{2\alpha}$-mediated disease responses, e.g., humans, cats, dogs and the like in an effective amount within the dosage range of about 0.1 to about 100 mg/kg, preferably about 0.2 to about 50 mg/kg and more preferably about 0.5 to about 0.5 to about 25 mg/kg (or from about 1 to about 2500 mg, preferably from about 5 to about 2000 mg) on a regimen in single or 2 to 4 divided daily doses.

The active ingredient can be utilized in a composition such as tablet, capsule, solution or suspension containing about 5 to about 500 mg per unit of dosage of a compound or mixture of compounds of formulas I, II or III in topical form for wound healing, etc. (0.01 to 5% by weight compound of formulas I, II or III, 1 to 5 treatments per day). They may be compounded in conventional matter with a physiologically acceptable vehicle or carrier, excipient, binder, preservative, stabilizer, flavor, etc., or with a topical

| STRUCTURE | $K_B$ (FP receptor) |
|---|---|
| 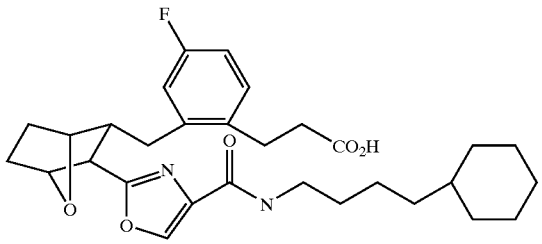 | 14.5 |
| 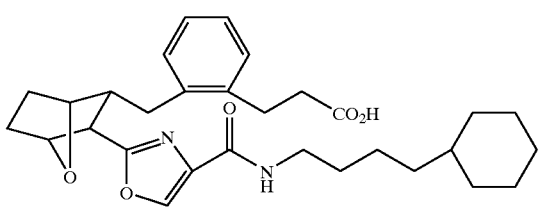 | 20.4 |
| 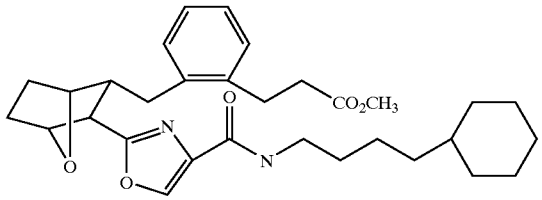 | 2410 |

The effects of the FP receptor antagonists disclosed above on the Ca2+ signal associated with FP receptor stimulation by the agonist 17-phenyl PGF$_{2\alpha}$ are depicted in FIGS. 4 through 6. The principal of this assay is that pretreatment with an antagonist will attenuate the response to agonist: this creates a rightward displacement of the 17-phenyl PGF$_{2\alpha}$ dose-response curve as illustrated.

carrier such as mineral oil as called for by accepted pharmaceutical practice.

The compounds of the invention may also be administered topically to treat peripheral vascular diseases and as such may be formulated as a cream or ointment.

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different pharmaceutical compositions may be prepared and used with substantially the same result. Thus, however detailed the foregoing may appear in text, it should not be construed as limiting the overall scope hereof; rather, the ambit of the present invention is to be governed only by the lawful construction of the appended claims.

What is claimed is:

1. A compound represented by the general formula I

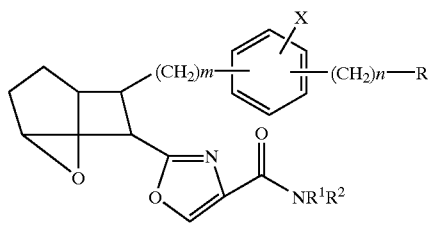

wherein m is an integer of from 1 to 3;

n is 0 or an integer of from 1 to 4;

R is selected from the group consisting of $CO_2H$, $CO_2R^6$, $CH_2OH$, $CH_2OR^6$

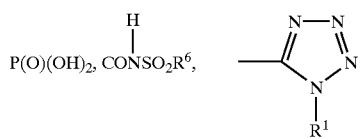

and $CONR^3R^4$;

$R^1$ and $R^2$ are independently selected from the group consisting of H, $R^6$, $C_1$–$C_6$ alkenyl, $C_1$–$C_6$ alkynyl, $C_3$–$C_7$ cycloalkyl, $C_4$–$C_{12}$ alkylcycloalkyl, $C_6$–$C_{10}$ aryl, $C_7$–$C_{12}$ alkyl aryl radicals an halogen-substituted derivatives of $R^1$ and $R^2$;

$R^3$ and $R^4$ are selected from the group consisting of H and $R^6$; and

X is selected from the group consisting of $R^6$, hydroxy, $N(R^6)_2$, $CON(R^6)_2$, $SR^6$, $COOR^6$, $NO_2$, CN and $OR^6$, wherein $R^6$ is $C_1$–$C_6$ alkyl, and pharmaceutically acceptable salts thereof.

2. The compounds of claim 1 represented by formula II

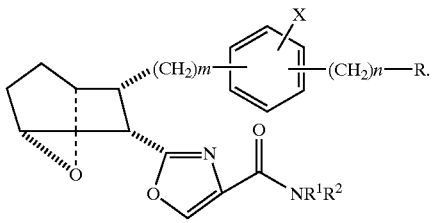

3. The compounds of claim 2 wherein m is 1 or 2.

4. The compounds of claim 2 wherein n is from 2 to 4.

5. The compounds of claim 2 wherein R is selected from the group consisting of $CO_2H$, $CO_2R^6$, $CH_2OH$, $CH_2OR^6$ and $CONR^3R^4$.

6. The compounds of claim 2 wherein R is selected from the group consisting of $CO_2H$ and $CO_2R^6$.

7. The compounds of claim 2 wherein $R^1$ and $R^2$ are selected from the group consisting of H, $R^6$, $C_3$–$C_7$ cycloalkyl and $C_4$–$C_{12}$ alkylcycloalkyl.

8. The compounds of claim 1 represented by formula III

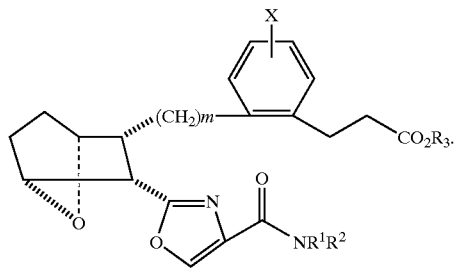

9. A pharmaceutical composition useful for treating $PGF_{2\alpha}$-mediated disease responses comprising as an active ingredient a compound of claim 1 and a pharmaceutically acceptable carrier.

10. The composition of claim 9 wherein said compound is a compound represented by formula II

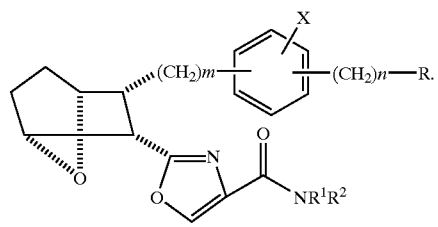

11. The composition of claim 10 wherein said compound is a compound wherein m is 1 or 2.

12. The composition of claim 10 wherein said compound is a compound wherein n is 2 or 4.

13. The composition of claim 10 wherein said compound is a compound wherein R is selected from the group consisting of $CO_2H$, $CO_2R_6$, $CH_2OH$, $CH_2OR^6$ and $CONR^3R^4$.

14. The composition of claim 13 wherein said compound is a compound wherein R is selected from the group consisting of $CO_2H$ and $CO_2R^6$.

15. The composition of claim 10 wherein said compound is a compound wherein $R^1$ and $R^2$ are selected from the group consisting of H, $R^6$, $C_3$–$C_7$ cycloalkyl and $C_4$–$C_{12}$ alkylcycloalkyl.

16. The composition of claim 9 wherein said compound is represented by formula III

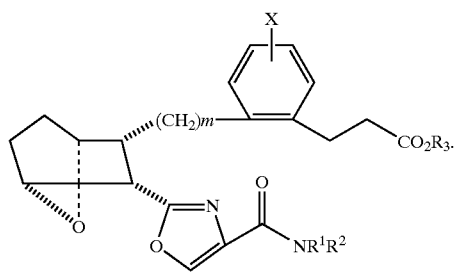

17. The pharmaceutical composition of claim 9 useful for treating inflammatory reactions relating to rheumatoid arthritis and psoriasis, reproductive disorders, bronchoconstrictive disorders, excessive bone breakdown, peptic ulcers, heart disease, platelet aggregation and thrombosis.

* * * * *